United States Patent [19]

Iizuka et al.

[11] Patent Number: 5,736,514
[45] Date of Patent: Apr. 7, 1998

[54] BACILLUS STRAIN AND HARMFUL ORGANISM CONTROLLING AGENTS

[75] Inventors: Toshihiko Iizuka, Sapporo; Michito Tagawa, Saitama-ken; Satoshi Arai, Saitama-ken; Masatsugu Niizeki, Saitama-ken; Toshiro Miyake, Saitama-ken, all of Japan

[73] Assignee: Nissan Chemical Industries, Ltd., Tokyo, Japan

[21] Appl. No.: 542,921

[22] Filed: Oct. 13, 1995

[30] Foreign Application Priority Data

Oct. 14, 1994 [JP] Japan ................................. 6-276082

[51] Int. Cl.$^6$ ........................ C07H 14/325; A01N 37/18
[52] U.S. Cl. .................... 514/12; 514/2; 530/350; 530/825
[58] Field of Search .................... 530/350, 825; 514/12, 2

[56] References Cited

FOREIGN PATENT DOCUMENTS 6-65292  3/1994  Japan .
WO 93/03154  2/1993  WIPO .
WO 94/05771  3/1994  WIPO .

OTHER PUBLICATIONS

Current Microbiology, vol. 30, No. 4, pp. 227–235, Apr. 1995, Katsutoshi Ogiwara, et al., "Nucleotide Sequence of the Gene Encoding Novel Delta–Endotoxin from *Bacillus Thuringiensis* Serovar Japonensis Strain Buibui Specific in Scarabaeid Beetles".

*Primary Examiner*—Robert A. Wax
*Assistant Examiner*—Gabriele E. Bugaisky
*Attorney, Agent, or Firm*—Oblon, Spivak, McClelland, Maier & Neustadt, P.C.

[57] ABSTRACT

A novel crystal protein as an effective ingredient in harmful organism controlling agents, *Bacillus thuringiensis* var. *japonensis* strain N141 producing the protein, and a gene coding for the protein. This novel strain produces an insecticidal crystal toxin and is useful for a harmful organism controlling agent.

4 Claims, 3 Drawing Sheets subsp. *japonensis* strain N141

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3759 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Bacillus thuringiensis var. japonensis
        ( B ) STRAIN: N141

( i x ) FEATURE:
( A ) NAME/KEY: CDS
( B ) LOCATION: 47..3556

( x i ) SEQUENCE DESCRIPTION: SEQ ID NO:1:

```
TTTTAAATAC ATTGGAGTGT AATAGACTGG TATTGGAGGA ACAAGT ATG AAT CGA    55
                                                   Met Asn Arg
                                                   1

AAT AAT CAA AAT GAA TAT GAA GTT ATT GAT GCC CCA CAT TGT GGG TGT   103
Asn Asn Gln Asn Glu Tyr Glu Val Ile Asp Ala Pro His Cys Gly Cys
    5                   10                  15

CCG GCA GAT GAT GTT GTA AAA TAT CCT TTG ACA GAT GAT CCG AAT GCT   151
Pro Ala Asp Asp Val Val Lys Tyr Pro Leu Thr Asp Asp Pro Asn Ala
20                  25                  30                  35

GGA TTG CAA AAT ATG AAC TAT AAG GAA TAT TTA CAA ACG TAT GGT GGA   199
Gly Leu Gln Asn Met Asn Tyr Lys Glu Tyr Leu Gln Thr Tyr Gly Gly
                40                  45                  50

GAC TAT ACA GAT CCT CTT ATT AAT CCT AAC TTA TCT GTT AGT GGA AAA   247
Asp Tyr Thr Asp Pro Leu Ile Asn Pro Asn Leu Ser Val Ser Gly Lys
            55                  60                  65

GAT GTA ATA CAA GTT GGA ATT AAT ATT GTA GGG AGA TTA CTA AGC TTT   295
Asp Val Ile Gln Val Gly Ile Asn Ile Val Gly Arg Leu Leu Ser Phe
        70                  75                  80

TTT GGA TTC CCC TTT TCT AGT CAA TGG GTT ACT GTA TAT ACC TAT CTT   343
Phe Gly Phe Pro Phe Ser Ser Gln Trp Val Thr Val Tyr Thr Tyr Leu
    85                  90                  95

TTA AAC AGC TTG TGG CCG GAT GAC GAG AAT TCT GTA TGG GAC GCT TTT   391
Leu Asn Ser Leu Trp Pro Asp Asp Glu Asn Ser Val Trp Asp Ala Phe
100                 105                 110                 115

ATG GAG AGA GTA GAA GAA CTT ATT GAT CAA AAA ATC TCA GAA GCA GTA   439
Met Glu Arg Val Glu Glu Leu Ile Asp Gln Lys Ile Ser Glu Ala Val
                120                 125                 130

AAG GGT AGG GCA TTG GAT GAC CTA ACT GGA TTA CAA TAT AAT TAT AAT   487
Lys Gly Arg Ala Leu Asp Asp Leu Thr Gly Leu Gln Tyr Asn Tyr Asn
            135                 140                 145

TTA TAT GTA GAA GCA TTA GAT GAG TGG CTG AAT AGA CCA AAT GGC GCA   535
Leu Tyr Val Glu Ala Leu Asp Glu Trp Leu Asn Arg Pro Asn Gly Ala
        150                 155                 160

AGG GCA TCC TTA GTT TCT CAG CGA TTT AAC ATT TTA GAT AGC CTA TTT   583
Arg Ala Ser Leu Val Ser Gln Arg Phe Asn Ile Leu Asp Ser Leu Phe
    165                 170                 175

ACA CAA TTT ATG CCA AGC TTT GGC TCT GGT CCT GGA AGT CAA AAT TAT   631
Thr Gln Phe Met Pro Ser Phe Gly Ser Gly Pro Gly Ser Gln Asn Tyr
180                 185                 190                 195
```

-continued

| | | | | | | | | | | | | | | | | |
|---|---|---|---|---|---|---|---|---|---|---|---|---|---|---|---|---|
| GCA | ACT | ATA | TTA | CTT | CCA | GTA | TAT | GCA | CAA | GCA | GCA | AAC | CTT | CAT | TTG | 679 |
| Ala | Thr | Ile | Leu | Leu | Pro | Val | Tyr | Ala | Gln | Ala | Ala | Asn | Leu | His | Leu | |
| | | | 200 | | | | | 205 | | | | | | 210 | | |
| TTA | TTA | TTA | AAA | GAT | GCA | GAC | ATT | TAT | GGA | GCT | AGA | TGG | GGG | CTG | AAT | 727 |
| Leu | Leu | Leu | Lys | Asp | Ala | Asp | Ile | Tyr | Gly | Ala | Arg | Trp | Gly | Leu | Asn | |
| | | | 215 | | | | 220 | | | | | | 225 | | | |
| CAA | ACT | CAA | ATA | GAT | CAA | TTC | CAT | TCT | CGT | CAA | CAA | AGC | CTT | ACT | CAG | 775 |
| Gln | Thr | Gln | Ile | Asp | Gln | Phe | His | Ser | Arg | Gln | Gln | Ser | Leu | Thr | Gln | |
| | | | 230 | | | | 235 | | | | | 240 | | | | |
| ACT | TAT | ACA | AAT | CAT | TGT | GTT | ACT | GCG | TAT | AAT | GAT | GGA | TTA | GCG | GAA | 823 |
| Thr | Tyr | Thr | Asn | His | Cys | Val | Thr | Ala | Tyr | Asn | Asp | Gly | Leu | Ala | Glu | |
| | 245 | | | | | 250 | | | | | 255 | | | | | |
| TTA | AGA | GGC | ACA | ACC | GCT | GAG | AGT | TGG | TTT | AAA | TAC | AAT | CAA | TAT | CGT | 871 |
| Leu | Arg | Gly | Thr | Thr | Ala | Glu | Ser | Trp | Phe | Lys | Tyr | Asn | Gln | Tyr | Arg | |
| 260 | | | | | 265 | | | | | 270 | | | | | 275 | |
| AGA | GAA | ATG | ACT | TTG | ACG | GCA | ATG | GAT | TTA | GTG | GCA | TTA | TTC | CCA | TAT | 919 |
| Arg | Glu | Met | Thr | Leu | Thr | Ala | Met | Asp | Leu | Val | Ala | Leu | Phe | Pro | Tyr | |
| | | | | 280 | | | | 285 | | | | | 290 | | | |
| TAT | AAT | TTA | CGA | CAA | TAT | CCA | GAT | GGG | ACA | AAT | CCT | CAA | CTT | ACA | CGT | 967 |
| Tyr | Asn | Leu | Arg | Gln | Tyr | Pro | Asp | Gly | Thr | Asn | Pro | Gln | Leu | Thr | Arg | |
| | | | 295 | | | | | 300 | | | | | 305 | | | |
| GAG | GTC | TAT | ACA | GAT | CCG | ATT | GCA | TTT | GAT | CCA | CTG | GAA | CAA | CCA | ACT | 1015 |
| Glu | Val | Tyr | Thr | Asp | Pro | Ile | Ala | Phe | Asp | Pro | Leu | Glu | Gln | Pro | Thr | |
| | | 310 | | | | | 315 | | | | | 320 | | | | |
| ACT | CAA | TTA | TGT | CGA | TCA | TGG | TAC | ATT | AAC | CCA | GCT | TTT | CGA | AAT | CAT | 1063 |
| Thr | Gln | Leu | Cys | Arg | Ser | Trp | Tyr | Ile | Asn | Pro | Ala | Phe | Arg | Asn | His | |
| 325 | | | | | 330 | | | | | 335 | | | | | | |
| TTG | AAT | TTC | TCT | GTA | CTA | GAA | AAT | TCA | TTG | ATT | CGT | CCC | CCG | CAC | CTT | 1111 |
| Leu | Asn | Phe | Ser | Val | Leu | Glu | Asn | Ser | Leu | Ile | Arg | Pro | Pro | His | Leu | |
| 340 | | | | | 345 | | | | | 350 | | | | | 355 | |
| TTT | GAA | AGG | TTA | AGT | AAT | TTG | CAA | ATT | TTA | GTT | AAT | TAC | CAA | ACA | AAC | 1159 |
| Phe | Glu | Arg | Leu | Ser | Asn | Leu | Gln | Ile | Leu | Val | Asn | Tyr | Gln | Thr | Asn | |
| | | | | 360 | | | | 365 | | | | | 370 | | | |
| GGT | AGC | GCT | TGG | CGT | GGG | TCA | AGG | GTA | AGA | TAC | CAT | TAT | TTG | CAT | AGT | 1207 |
| Gly | Ser | Ala | Trp | Arg | Gly | Ser | Arg | Val | Arg | Tyr | His | Tyr | Leu | His | Ser | |
| | | | 375 | | | | 380 | | | | | 385 | | | | |
| TCT | ATA | ATA | CAG | GAA | AAA | AGT | TAC | GGC | CTC | CTC | AGT | GAT | CCC | GTT | GGA | 1255 |
| Ser | Ile | Ile | Gln | Glu | Lys | Ser | Tyr | Gly | Leu | Leu | Ser | Asp | Pro | Val | Gly | |
| | | 390 | | | | | 395 | | | | | 400 | | | | |
| GCT | AAT | ATC | AAT | GTT | CAA | AAT | AAT | GAT | ATT | TAT | CAG | ATT | ATT | TCG | CAG | 1303 |
| Ala | Asn | Ile | Asn | Val | Gln | Asn | Asn | Asp | Ile | Tyr | Gln | Ile | Ile | Ser | Gln | |
| | | 405 | | | | 410 | | | | | 415 | | | | | |
| GTT | AGC | AAT | TTT | GCT | AGT | CCT | GTT | GGC | TCA | TCA | TAT | AGT | GTT | TGG | GAC | 1351 |
| Val | Ser | Asn | Phe | Ala | Ser | Pro | Val | Gly | Ser | Ser | Tyr | Ser | Val | Trp | Asp | |
| 420 | | | | | 425 | | | | 430 | | | | | | 435 | |
| ACT | AAC | TTT | TAT | TTG | AGT | TCA | GGA | CAA | GTA | AGT | GGG | ATT | TCA | GGA | TAT | 1399 |
| Thr | Asn | Phe | Tyr | Leu | Ser | Ser | Gly | Gln | Val | Ser | Gly | Ile | Ser | Gly | Tyr | |
| | | | | 440 | | | | 445 | | | | | 450 | | | |
| ACA | CAG | CAA | GGT | ATA | CCA | GCA | GTT | TGT | CTT | CAA | CAA | CGA | AAT | TCA | ACT | 1447 |
| Thr | Gln | Gln | Gly | Ile | Pro | Ala | Val | Cys | Leu | Gln | Gln | Arg | Asn | Ser | Thr | |
| | | | 455 | | | | 460 | | | | | 465 | | | | |
| GAT | GAG | TTA | CCA | AGC | TTA | AAT | CCG | GAA | GGA | GAT | ATC | ATT | AGA | AAT | TAT | 1495 |
| Asp | Glu | Leu | Pro | Ser | Leu | Asn | Pro | Glu | Gly | Asp | Ile | Ile | Arg | Asn | Tyr | |
| | | 470 | | | | 475 | | | | | 480 | | | | | |
| AGT | CAT | AGG | TTA | TCT | CAT | ATA | ACC | CAA | TAT | CGT | TTT | CAA | GCA | ACT | CAA | 1543 |
| Ser | His | Arg | Leu | Ser | His | Ile | Thr | Gln | Tyr | Arg | Phe | Gln | Ala | Thr | Gln | |
| | 485 | | | | | 490 | | | | | 495 | | | | | |
| AGT | GGT | AGT | CCA | TCA | ACT | GTT | AGC | GCA | AAT | TTA | CCT | ACT | TGT | GTA | TGG | 1591 |
| Ser | Gly | Ser | Pro | Ser | Thr | Val | Ser | Ala | Asn | Leu | Pro | Thr | Cys | Val | Trp | |
| 500 | | | | | 505 | | | | | 510 | | | | | 515 | |

-continued

| | | | | | | | | | | | | | | | | |
|---|---|---|---|---|---|---|---|---|---|---|---|---|---|---|---|---|
| ACG | CAT | CGA | GAT | GTG | GAC | CTT | GAT | AAT | ACC | ATT | ACT | GCG | AAT | CAA | ATT | 1639 |
| Thr | His | Arg | Asp | Val<br>520 | Asp | Leu | Asp | Asn | Thr<br>525 | Ile | Thr | Ala | Asn | Gln<br>530 | Ile | |
| ACA | CAA | CTA | CCA | TTA | GTA | AAG | GCA | TAT | GAG | CTA | AGT | AGT | GGT | GCT | ACT | 1687 |
| Thr | Gln | Leu | Pro<br>535 | Leu | Val | Lys | Ala | Tyr | Glu<br>540 | Leu | Ser | Ser | Gly<br>545 | Ala | Thr | |
| GTC | GTG | AAA | GGT | CCA | GGA | TTC | ACA | GGA | GGA | GAT | GTA | ATC | CGA | AGA | ACA | 1735 |
| Val | Val | Lys<br>550 | Gly | Pro | Gly | Phe | Thr<br>555 | Gly | Gly | Asp | Val | Ile<br>560 | Arg | Arg | Thr | |
| AAT | ACT | GGT | GGA | TTC | GGA | GCA | ATA | AGG | GTG | TCG | GTC | ACT | GGA | CCG | CTA | 1783 |
| Asn | Thr<br>565 | Gly | Gly | Phe | Gly | Ala<br>570 | Ile | Arg | Val | Ser | Val<br>575 | Thr | Gly | Pro | Leu | |
| ACA | CAA | CGA | TAT | CGC | ATA | AGG | TTC | CGT | TAT | GCT | TCG | ACA | ATA | GAT | TTT | 1831 |
| Thr<br>580 | Gln | Arg | Tyr | Arg | Ile<br>585 | Arg | Phe | Arg | Tyr | Ala<br>590 | Ser | Thr | Ile | Asp | Phe<br>595 | |
| GAT | TTC | TTT | GTA | ACA | CGT | GGA | GGA | ACT | ACT | ATA | AAT | AAT | TTT | AGA | TTT | 1879 |
| Asp | Phe | Phe | Val | Thr<br>600 | Arg | Gly | Gly | Thr | Thr<br>605 | Ile | Asn | Asn | Phe | Arg<br>610 | Phe | |
| ACA | CGT | ACA | ATG | AAC | AGG | GGA | CAG | GAA | TCA | AGA | TAT | GAA | TCC | TAT | CGT | 1927 |
| Thr | Arg | Thr | Met<br>615 | Asn | Arg | Gly | Gln | Glu<br>620 | Ser | Arg | Tyr | Glu | Ser<br>625 | Tyr | Arg | |
| ACT | GTA | GAG | TTT | ACA | ACT | CCT | TTT | AAC | TTT | ACA | CAA | AGT | CAA | GAT | ATA | 1975 |
| Thr | Val | Glu<br>630 | Phe | Thr | Thr | Pro | Phe<br>635 | Asn | Phe | Thr | Gln | Ser<br>640 | Gln | Asp | Ile | |
| ATT | CGA | ACA | TCT | ATC | CAG | GGA | CTT | AGT | GGA | AAT | GGG | GAA | GTA | TAC | CTT | 2023 |
| Ile | Arg<br>645 | Thr | Ser | Ile | Gln | Gly<br>650 | Leu | Ser | Gly | Asn | Gly<br>655 | Glu | Val | Tyr | Leu | |
| GAT | AGA | ATT | GAA | ATC | ATC | CCT | GTG | AAC | CCG | GCA | CGA | GAA | GCA | GAA | GAG | 2071 |
| Asp | Arg | Ile | Glu | Ile<br>660 | Ile | Pro | Val | Asn | Pro<br>665 | Ala | Arg | Glu | Ala<br>670 | Glu | Glu<br>675 | |
| GAT | TTA | GAA | GCA | GCG | AAG | AAA | GCG | GCT | AGG | CAG | AAC | TTG | TTT | ACA | CGT | 2119 |
| Asp | Leu | Glu | Ala | Ala<br>680 | Lys | Lys | Ala | Ala | Arg<br>685 | Gln | Asn | Leu | Phe | Thr<br>690 | Arg | |
| ACA | AGG | GAC | GGA | TTA | CAG | GTA | AAT | GTG | ACA | GAT | TAT | CAA | GTG | GAC | CAA | 2167 |
| Thr | Arg | Asp | Gly<br>695 | Leu | Gln | Val | Asn | Val<br>700 | Thr | Asp | Tyr | Gln | Val<br>705 | Asp | Gln | |
| GCG | GCA | AAT | TTA | GTG | TCA | TGC | TTA | TCC | GAT | GAA | CAA | TAT | GGG | CAT | GAC | 2215 |
| Ala | Ala | Asn<br>710 | Leu | Val | Ser | Cys | Leu<br>715 | Ser | Asp | Glu | Gln | Tyr<br>720 | Gly | His | Asp | |
| AAA | AAG | ATG | TTA | TTG | GAA | GCG | GTA | AGA | GCG | GCA | AAA | CGC | CTC | AGC | CGC | 2263 |
| Lys | Lys<br>725 | Met | Leu | Leu | Glu | Ala<br>730 | Val | Arg | Ala | Ala | Lys<br>735 | Arg | Leu | Ser | Arg | |
| GAA | CGC | AAC | TTA | CTT | CAA | GAT | CCA | GAT | TTT | AAT | ACA | ATC | AAT | AGT | ACA | 2311 |
| Glu | Arg | Asn<br>740 | Leu | Leu | Gln | Asp | Pro<br>745 | Asp | Phe | Asn | Thr | Ile<br>750 | Asn | Ser | Thr<br>755 | |
| GAA | GAG | AAT | GGC | TGG | AAG | GCA | AGT | AAC | GGT | GTT | ACT | ATT | AGC | GAG | GGC | 2359 |
| Glu | Glu | Asn | Gly | Trp<br>760 | Lys | Ala | Ser | Asn | Gly<br>765 | Val | Thr | Ile | Ser | Glu<br>770 | Gly | |
| GGT | CCA | TTC | TTT | AAA | GGT | CGT | GCA | CTT | CAG | TTA | GCA | AGC | GCA | AGA | GAA | 2407 |
| Gly | Pro | Phe<br>775 | Phe | Lys | Gly | Arg | Ala<br>780 | Leu | Gln | Leu | Ala | Ser<br>785 | Ala | Arg | Glu | |
| AAT | TAT | CCA | ACA | TAC | ATT | TAT | CAA | AAA | GTA | GAT | GCA | TCG | GTG | TTA | AAG | 2455 |
| Asn | Tyr | Pro<br>790 | Thr | Tyr | Ile | Tyr | Gln<br>795 | Lys | Val | Asp | Ala | Ser<br>800 | Val | Leu | Lys | |
| CCT | TAT | ACA | CGC | TAT | AGA | CTG | GAT | GGG | TTC | GTG | AAG | AGT | AGT | CAA | GAT | 2503 |
| Pro | Tyr | Thr<br>805 | Arg | Tyr | Arg | Leu | Asp<br>810 | Gly | Phe | Val | Lys | Ser<br>815 | Ser | Gln | Asp | |
| TTA | GAA | ATT | GAT | CTC | ATT | CAC | TAT | CAT | AAA | GTC | CAT | CTT | GTG | AAA | AAT | 2551 |
| Leu<br>820 | Glu | Ile | Asp | Leu | Ile<br>825 | His | Tyr | His | Lys | Val<br>830 | His | Leu | Val | Lys | Asn<br>835 | |

```
GTA CCA GAT AAT TTA GTA TCC GAT ACT TAC TCG GAT GGT TCT TGC AGT      2599
Val Pro Asp Asn Leu Val Ser Asp Thr Tyr Ser Asp Gly Ser Cys Ser
            840             845             850

GGA ATG AAT CGA TGT GAG GAA CAA CAG ATG GTA AAT GCG CAA CTG GAA      2647
Gly Met Asn Arg Cys Glu Glu Gln Gln Met Val Asn Ala Gln Leu Glu
        855             860             865

ACA GAA CAT CAT CAT CCG ATG GAT TGC TGT GAA GCG GCT CAA ACA CAT      2695
Thr Glu His His His Pro Met Asp Cys Cys Glu Ala Ala Gln Thr His
        870             875             880

GAG TTT TCT TCC TAT ATT AAT ACA GGG GAT CTA AAT GCA AGT GTA GAT      2743
Glu Phe Ser Ser Tyr Ile Asn Thr Gly Asp Leu Asn Ala Ser Val Asp
885             890             895

CAG GGC ATT TGG GTT GTA TTA AAA GTT CGA ACA ACA GAT GGG TAT GCG      2791
Gln Gly Ile Trp Val Val Leu Lys Val Arg Thr Thr Asp Gly Tyr Ala
900             905             910             915

ACG TTA GGA AAT CTT GAA TTG GTA GAG GTT GGG CCA TTA TCG GGT GAA      2839
Thr Leu Gly Asn Leu Glu Leu Val Glu Val Gly Pro Leu Ser Gly Glu
            920             925             930

TCT CTA GAA CGG GAA CAA AGA GAT AAT GCG AAA TGG AAT GCA GAG CTA      2887
Ser Leu Glu Arg Glu Gln Arg Asp Asn Ala Lys Trp Asn Ala Glu Leu
        935             940             945

GGA AGA AAA CGT GCA GAA ATA GAT CGT GTG TAT TTA GCT GCG AAA CAA      2935
Gly Arg Lys Arg Ala Glu Ile Asp Arg Val Tyr Leu Ala Ala Lys Gln
        950             955             960

GCA ATT AAT CAT CTG TTT GTA GAC TAT CAA GAT CAA CAA TTA AAT CCA      2983
Ala Ile Asn His Leu Phe Val Asp Tyr Gln Asp Gln Gln Leu Asn Pro
965             970             975

GAA ATT GGG CTA GCA GAA ATT AAT GAA GCT TCA AAT CTT GTA GAG TCA      3031
Glu Ile Gly Leu Ala Glu Ile Asn Glu Ala Ser Asn Leu Val Glu Ser
980             985             990             995

ATT TCG GGT GTA TAT AGT GAT ACA CTA TTA CAG ATT CCT GGG ATT AAC      3079
Ile Ser Gly Val Tyr Ser Asp Thr Leu Leu Gln Ile Pro Gly Ile Asn
            1000            1005            1010

TAC GAA ATT TAC ACA GAG TTA TCC GAT CGC TTA CAA CAA GCA TCG TAT      3127
Tyr Glu Ile Tyr Thr Glu Leu Ser Asp Arg Leu Gln Gln Ala Ser Tyr
        1015            1020            1025

CTG TAT ACG TCT CGA AAT GCG GTG CAA AAT GGA GAC TTT AAC AGT GGT      3175
Leu Tyr Thr Ser Arg Asn Ala Val Gln Asn Gly Asp Phe Asn Ser Gly
        1030            1035            1040

CTA GAT AGT TGG AAT ACA ACT ACG GAT GCA TCG GTT CAG CAA GAT GGC      3223
Leu Asp Ser Trp Asn Thr Thr Thr Asp Ala Ser Val Gln Gln Asp Gly
1045            1050            1055

AAT ATG CAT TTC TTA GTT CTT TCG CAT TGG GAT GCA CAA GTT TCT CAA      3271
Asn Met His Phe Leu Val Leu Ser His Trp Asp Ala Gln Val Ser Gln
1060            1065            1070            1075

CAA TTG AGA GTA AAT CCG AAT TGT AAG TAT GTC TTA CGT GTG ACA GCA      3319
Gln Leu Arg Val Asn Pro Asn Cys Lys Tyr Val Leu Arg Val Thr Ala
        1080            1085            1090

AGA AAA GTA GGA GGC GGA GAT GGA TAC GTC ACA ATC CGA GAT GGC GCT      3367
Arg Lys Val Gly Gly Gly Asp Gly Tyr Val Thr Ile Arg Asp Gly Ala
            1095            1100            1105

CAT CAC CAA GAA ACT CTT ACA TTT AAT GCA TGT GAC TAC GAT GTA AAT      3415
His His Gln Glu Thr Leu Thr Phe Asn Ala Cys Asp Tyr Asp Val Asn
        1110            1115            1120

GGT ACG TAT GTC AAT GAC AAT TCG TAT ATA ACA GAA GAA GTG GTA TTC      3463
Gly Thr Tyr Val Asn Asp Asn Ser Tyr Ile Thr Glu Glu Val Val Phe
        1125            1130            1135

TAC CCA GAG ACA AAA CAT ATG TGG GTA GAG GTG AGT GAA TCC GAA GGT      3511
Tyr Pro Glu Thr Lys His Met Trp Val Glu Val Ser Glu Ser Glu Gly
1140            1145            1150            1155
```

```
TCA TTC TAT ATA GAC AGT ATT GAG TTT ATT GAA ACA CAA GAG TAG                3556
Ser Phe Tyr Ile Asp Ser Ile Glu Phe Ile Glu Thr Gln Glu *
            1160            1165                    1170

AAGAGGGGGA TCCTAACGTA TAGCAACTAT GAGAGGATAC TCCGTACAAA CAAAGATTAA          3616

AAAAAGGTAA AATGAATAGA ACCCCCTACT GGTAGAAGGT CTGGTAGGGG GTTCTTACAT          3676

GAAAAAATGT AGCTGTTTAC TAAGGTATAT AAAAAACAGC ATATTTGATA GAAAAAAATG          3736

AGTACCTTAT AAAGAAGAA TTC                                                   3759
```

( 2 ) INFORMATION FOR SEQ ID NO:2:

( i ) SEQUENCE CHARACTERISTICS:
        ( A ) LENGTH: 1169 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Arg Asn Asn Gln Asn Glu Tyr Glu Val Ile Asp Ala Pro His
 1               5                  10                  15

Cys Gly Cys Pro Ala Asp Asp Val Val Lys Tyr Pro Leu Thr Asp Asp
            20                  25                  30

Pro Asn Ala Gly Leu Gln Asn Met Asn Tyr Lys Glu Tyr Leu Gln Thr
            35                  40                  45

Tyr Gly Gly Asp Tyr Thr Asp Pro Leu Ile Asn Pro Asn Leu Ser Val
    50                  55                  60

Ser Gly Lys Asp Val Ile Gln Val Gly Ile Asn Ile Val Gly Arg Leu
65                  70                  75                  80

Leu Ser Phe Phe Gly Phe Pro Phe Ser Ser Gln Trp Val Thr Val Tyr
                85                  90                  95

Thr Tyr Leu Leu Asn Ser Leu Trp Pro Asp Asp Glu Asn Ser Val Trp
            100                 105                 110

Asp Ala Phe Met Glu Arg Val Glu Glu Leu Ile Asp Gln Lys Ile Ser
            115                 120                 125

Glu Ala Val Lys Gly Arg Ala Leu Asp Asp Leu Thr Gly Leu Gln Tyr
    130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
            180                 185                 190

Gln Asn Tyr Ala Thr Ile Leu Leu Pro Val Tyr Ala Gln Ala Ala Asn
    195                 200                 205

Leu His Leu Leu Leu Leu Lys Asp Ala Asp Ile Tyr Gly Ala Arg Trp
210                 215                 220

Gly Leu Asn Gln Thr Gln Ile Asp Gln Phe His Ser Arg Gln Gln Ser
225                 230                 235                 240

Leu Thr Gln Thr Tyr Thr Asn His Cys Val Thr Ala Tyr Asn Asp Gly
                245                 250                 255

Leu Ala Glu Leu Arg Gly Thr Thr Ala Glu Ser Trp Phe Lys Tyr Asn
            260                 265                 270

Gln Tyr Arg Arg Glu Met Thr Leu Thr Ala Met Asp Leu Val Ala Leu
    275                 280                 285

Phe Pro Tyr Tyr Asn Leu Arg Gln Tyr Pro Asp Gly Thr Asn Pro Gln
290                 295                 300
```

| | | | | | | | | | | | | | | |
|---|---|---|---|---|---|---|---|---|---|---|---|---|---|---|
| Leu | Thr | Arg | Glu | Val | Tyr | Thr | Asp | Pro | Ile | Ala | Phe | Asp | Pro | Leu | Glu |
| 305 | | | | | 310 | | | | | 315 | | | | | 320 |
| Gln | Pro | Thr | Thr | Gln | Leu | Cys | Arg | Ser | Trp | Tyr | Ile | Asn | Pro | Ala | Phe |
| | | | | 325 | | | | | 330 | | | | | 335 | |
| Arg | Asn | His | Leu | Asn | Phe | Ser | Val | Leu | Glu | Asn | Ser | Leu | Ile | Arg | Pro |
| | | | 340 | | | | | 345 | | | | | 350 | | |
| Pro | His | Leu | Phe | Glu | Arg | Leu | Ser | Asn | Leu | Gln | Ile | Leu | Val | Asn | Tyr |
| | | 355 | | | | | 360 | | | | | 365 | | | |
| Gln | Thr | Asn | Gly | Ser | Ala | Trp | Arg | Gly | Ser | Arg | Val | Arg | Tyr | His | Tyr |
| | 370 | | | | | 375 | | | | | 380 | | | | |
| Leu | His | Ser | Ser | Ile | Ile | Gln | Glu | Lys | Ser | Tyr | Gly | Leu | Leu | Ser | Asp |
| 385 | | | | | 390 | | | | | 395 | | | | | 400 |
| Pro | Val | Gly | Ala | Asn | Ile | Asn | Val | Gln | Asn | Asn | Asp | Ile | Tyr | Gln | Ile |
| | | | | 405 | | | | | 410 | | | | | 415 | |
| Ile | Ser | Gln | Val | Ser | Asn | Phe | Ala | Ser | Pro | Val | Gly | Ser | Ser | Tyr | Ser |
| | | | 420 | | | | | 425 | | | | | 430 | | |
| Val | Trp | Asp | Thr | Asn | Phe | Tyr | Leu | Ser | Ser | Gly | Gln | Val | Ser | Gly | Ile |
| | | | 435 | | | | | 440 | | | | | 445 | | |
| Ser | Gly | Tyr | Thr | Gln | Gln | Gly | Ile | Pro | Ala | Val | Cys | Leu | Gln | Gln | Arg |
| | 450 | | | | | 455 | | | | | 460 | | | | |
| Asn | Ser | Thr | Asp | Glu | Leu | Pro | Ser | Leu | Asn | Pro | Glu | Gly | Asp | Ile | Ile |
| 465 | | | | | 470 | | | | | 475 | | | | | 480 |
| Arg | Asn | Tyr | Ser | His | Arg | Leu | Ser | His | Ile | Thr | Gln | Tyr | Arg | Phe | Gln |
| | | | | 485 | | | | | 490 | | | | | 495 | |
| Ala | Thr | Gln | Ser | Gly | Ser | Pro | Ser | Thr | Val | Ser | Ala | Asn | Leu | Pro | Thr |
| | | | 500 | | | | | 505 | | | | | 510 | | |
| Cys | Val | Trp | Thr | His | Arg | Asp | Val | Asp | Leu | Asp | Asn | Thr | Ile | Thr | Ala |
| | | | 515 | | | | | 520 | | | | | 525 | | |
| Asn | Gln | Ile | Thr | Gln | Leu | Pro | Leu | Val | Lys | Ala | Tyr | Glu | Leu | Ser | Ser |
| | 530 | | | | | 535 | | | | | 540 | | | | |
| Gly | Ala | Thr | Val | Val | Lys | Gly | Pro | Gly | Phe | Thr | Gly | Gly | Asp | Val | Ile |
| 545 | | | | | 550 | | | | | 555 | | | | | 560 |
| Arg | Arg | Thr | Asn | Thr | Gly | Gly | Phe | Gly | Ala | Ile | Arg | Val | Ser | Val | Thr |
| | | | | 565 | | | | | 570 | | | | | 575 | |
| Gly | Pro | Leu | Thr | Gln | Arg | Tyr | Arg | Ile | Arg | Phe | Arg | Tyr | Ala | Ser | Thr |
| | | | 580 | | | | | 585 | | | | | 590 | | |
| Ile | Asp | Phe | Asp | Phe | Phe | Val | Thr | Arg | Gly | Gly | Thr | Thr | Ile | Asn | Asn |
| | | 595 | | | | | 600 | | | | | 605 | | | |
| Phe | Arg | Phe | Thr | Arg | Thr | Met | Asn | Arg | Gly | Gln | Glu | Ser | Arg | Tyr | Glu |
| | 610 | | | | | 615 | | | | | 620 | | | | |
| Ser | Tyr | Arg | Thr | Val | Glu | Phe | Thr | Thr | Pro | Phe | Asn | Phe | Thr | Gln | Ser |
| 625 | | | | | 630 | | | | | 635 | | | | | 640 |
| Gln | Asp | Ile | Ile | Arg | Thr | Ser | Ile | Gln | Gly | Leu | Ser | Gly | Asn | Gly | Glu |
| | | | | 645 | | | | | 650 | | | | | 655 | |
| Val | Tyr | Leu | Asp | Arg | Ile | Glu | Ile | Ile | Pro | Val | Asn | Pro | Ala | Arg | Glu |
| | | | 660 | | | | | 665 | | | | | 670 | | |
| Ala | Glu | Glu | Asp | Leu | Glu | Ala | Ala | Lys | Lys | Ala | Ala | Arg | Gln | Asn | Leu |
| | | 675 | | | | | 680 | | | | | 685 | | | |
| Phe | Thr | Arg | Thr | Arg | Asp | Gly | Leu | Gln | Val | Asn | Val | Thr | Asp | Tyr | Gln |
| | 690 | | | | | 695 | | | | | 700 | | | | |
| Val | Asp | Gln | Ala | Ala | Asn | Leu | Val | Ser | Cys | Leu | Ser | Asp | Glu | Gln | Tyr |
| 705 | | | | | 710 | | | | | 715 | | | | | 720 |
| Gly | His | Asp | Lys | Lys | Met | Leu | Leu | Glu | Ala | Val | Arg | Ala | Ala | Lys | Arg |

-continued

|     |     |     | 725 |     |     |     |     | 730 |     |     |     |     | 735 |     |
| --- | --- | --- | --- | --- | --- | --- | --- | --- | --- | --- | --- | --- | --- | --- |

Leu Ser Arg Glu Arg Asn Leu Leu Gln Asp Pro Asp Phe Asn Thr Ile
            740                 745                 750

Asn Ser Thr Glu Glu Asn Gly Trp Lys Ala Ser Asn Gly Val Thr Ile
            755                 760                 765

Ser Glu Gly Gly Pro Phe Phe Lys Gly Arg Ala Leu Gln Leu Ala Ser
        770             775             780

Ala Arg Glu Asn Tyr Pro Thr Tyr Ile Tyr Gln Lys Val Asp Ala Ser
785             790                 795                     800

Val Leu Lys Pro Tyr Thr Arg Tyr Arg Leu Asp Gly Phe Val Lys Ser
                805                 810                 815

Ser Gln Asp Leu Glu Ile Asp Leu Ile His Tyr His Lys Val His Leu
            820                 825                 830

Val Lys Asn Val Pro Asp Asn Leu Val Ser Asp Thr Tyr Ser Asp Gly
        835                 840             845

Ser Cys Ser Gly Met Asn Arg Cys Glu Glu Gln Met Val Asn Ala
        850             855             860

Gln Leu Glu Thr Glu His His Pro Met Asp Cys Cys Glu Ala Ala
865             870             875                     880

Gln Thr His Glu Phe Ser Ser Tyr Ile Asn Thr Gly Asp Leu Asn Ala
                885             890                 895

Ser Val Asp Gln Gly Ile Trp Val Val Leu Lys Val Arg Thr Thr Asp
            900             905             910

Gly Tyr Ala Thr Leu Gly Asn Leu Glu Leu Val Glu Val Gly Pro Leu
        915             920             925

Ser Gly Glu Ser Leu Glu Arg Glu Gln Arg Asp Asn Ala Lys Trp Asn
930                 935             940

Ala Glu Leu Gly Arg Lys Arg Ala Glu Ile Asp Arg Val Tyr Leu Ala
945                 950                 955                 960

Ala Lys Gln Ala Ile Asn His Leu Phe Val Asp Tyr Gln Asp Gln Gln
                965             970             975

Leu Asn Pro Glu Ile Gly Leu Ala Glu Ile Asn Glu Ala Ser Asn Leu
            980             985             990

Val Glu Ser Ile Ser Gly Val Tyr Ser Asp Thr Leu Leu Gln Ile Pro
            995                 1000                1005

Gly Ile Asn Tyr Glu Ile Tyr Thr Glu Leu Ser Asp Arg Leu Gln Gln
    1010            1015               1020

Ala Ser Tyr Leu Tyr Thr Ser Arg Asn Ala Val Gln Asn Gly Asp Phe
1025            1030                1035                1040

Asn Ser Gly Leu Asp Ser Trp Asn Thr Thr Thr Asp Ala Ser Val Gln
                1045                1050            1055

Gln Asp Gly Asn Met His Phe Leu Val Leu Ser His Trp Asp Ala Gln
            1060                1065            1070

Val Ser Gln Gln Leu Arg Val Asn Pro Asn Cys Lys Tyr Val Leu Arg
        1075            1080                1085

Val Thr Ala Arg Lys Val Gly Gly Gly Asp Gly Tyr Val Thr Ile Arg
        1090            1095            1100

Asp Gly Ala His His Gln Glu Thr Leu Thr Phe Asn Ala Cys Asp Tyr
1105            1110               1115                1120

Asp Val Asn Gly Thr Tyr Val Asn Asp Asn Ser Tyr Ile Thr Glu Glu
                1125                1130                1135

Val Val Phe Tyr Pro Glu Thr Lys His Met Trp Val Glu Val Ser Glu
            1140                1145                1150

-continued

| Ser | Glu | Gly | Ser | Phe | Tyr | Ile | Asp | Ser | Ile | Glu | Phe | Ile | Glu | Thr | Gln |
|     | 1155 |     |     |     |     |     | 1160 |     |     |     |     |     | 1165 |     |     |
| Glu | * |
|     | 1170 |

BACILLUS STRAIN AND HARMFUL ORGANISM CONTROLLING AGENTS

FIELD OF THE INVENTION

The present invention relates to novel *Bacillus thuringiensis* var. *japonensis* strain N141, hereinafter sometimes abbreviated as N141, an insecticidal crystal protein produced thereby, a gene coding for the protein, and a harmful organism controlling agent comprising the protein.

BACKGROUND OF THE INVENTION

*Bacillus thuringiensis*, hereinafter abbreviated as Bt, and crystalline toxic proteins produced thereby are very useful as microbial pesticides, which do not pollute the environment (Bt agents), particularly as insecticides against lepidopterous insect pests, and in practice have been widely used in the world.

Bt is a gram-positive bacilliform bacterium which produces a crystal protein at the sporulation stage in the end of the logarithmic growth phase. When orally taken into the mid-gut of an insect, the crystal protein will be subjected to alkaline and enzymatic activation in the digestive juice to show insecticidal activities accompanied with paralyses. However, the protein does not show any toxicity to mammals. The crystal proteins produced by Bt are generally of so-called diamond-shaped, bipyramidal or rhomboidal form. These crystal proteins are formed with endospores in the sporangium and released from the sporangium together with the endospores (Hannay, C. L.; Nature, 172, 1004 (1953)).

Bt has been classified on the basis of H-antigen according to the proposal by De Barjac and Bonefoi (Entomophaga, 7, 5–31 (1962)). A large number of subspecies have been found up to now.

The insecticidal activities of these strains are highly specific and may vary with subspecies. For example, it has been known that the subspecies *kurustaki* and *aizawai* show activities against lepidopterous insects while other subspecies *tenebrionis* and *japonensis buibui* are active against coleopterous insects.

In practice, however, each of strains belonging to the same subspecies has a different insecticidal activity spectrum. Some of lepidopterous pests may have acquired resistance to the Bt strain which showed an activity against the lepidopterous pests. Further, few strains have been reported which show an effective activity against coleopterous insects.

Thus, novel Bt agents would be desirable which are also effective against the lepidopterous pests having resistance to some known Bt agents. Also, there is a need for Bt agents having an activity against coleopterous insects.

SUMMARY OF THE INVENTION

The present inventors have found a novel strain producing a crystalline protein which has an excellent insecticidal activity against lepidopterous and coleopterous insects and attained the present invention.

Accordingly, the present invention is concerned with a novel strain N141 of *Bacillus thuringiensis* var. *japonensis* which has been originally deposited at National Institute of Bioscience and Human-Technology (NIBH), Agency of Industrial Science and Technology, Ministry of International Trade and Industry, Tsukuba, Japan on Oct. 6, 1994 under Accession Number FERM P-14576. This strain has been transferred to the deposit under Budapest Treaty conditions on Sep. 25, 1995 under Accession Number FERM BP-5241.

According to another aspect of the present invention, there is provided a harmful organism controlling agent comprising as a main ingredient an insecticidal crystal protein produced by N141, hereinafter abbreviated as N141 crystal protein. Further, the present invention provides a method of protecting a plant from damage caused by a pest which comprises applying the pest with the N141 crystal protein.

DESCRIPTION OF THE INVENTION

The novel strain N141 was isolated by a conventional method for isolating a bacterium of the genus Bacillus forming thermostable spores. Namely, a suspension of soil taken in Saitama, Japan was subjected to heat treatment at 50° to 90° C. and cultivated in a standard plating medium such as NB plate media to isolate the strain.

Features of the novel strain N141

Colony formation: An opaque white colony with an irregular border.

Cell morphology in the growth phase: Typical of Bt.

Serotype of H-antigen: 23, *japonensis*.

Figure 1:
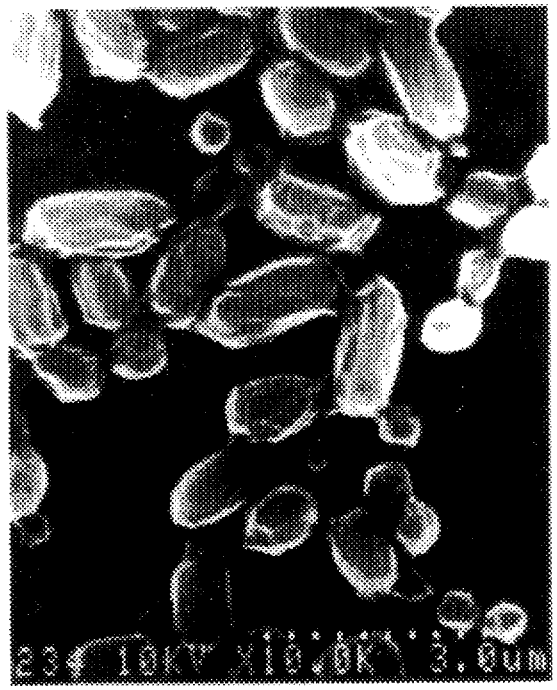
FIG. 1 is an electron microscopic photograph of *Bacillus thuringiensis* var. *japonensis* strain N141.

Intracellular component: A sporulating cell produces an amorphous crystal protein. The electron microscopic photograph of the crystal protein is shown in FIG. 1.

Alkali-soluble protein: This strain has a protein which runs to about 130,000 daltons on electrophoresis.

Activity: This strain has an insecticidal activity against lepidopterous and coleopterous pests tested.

Figure 2:
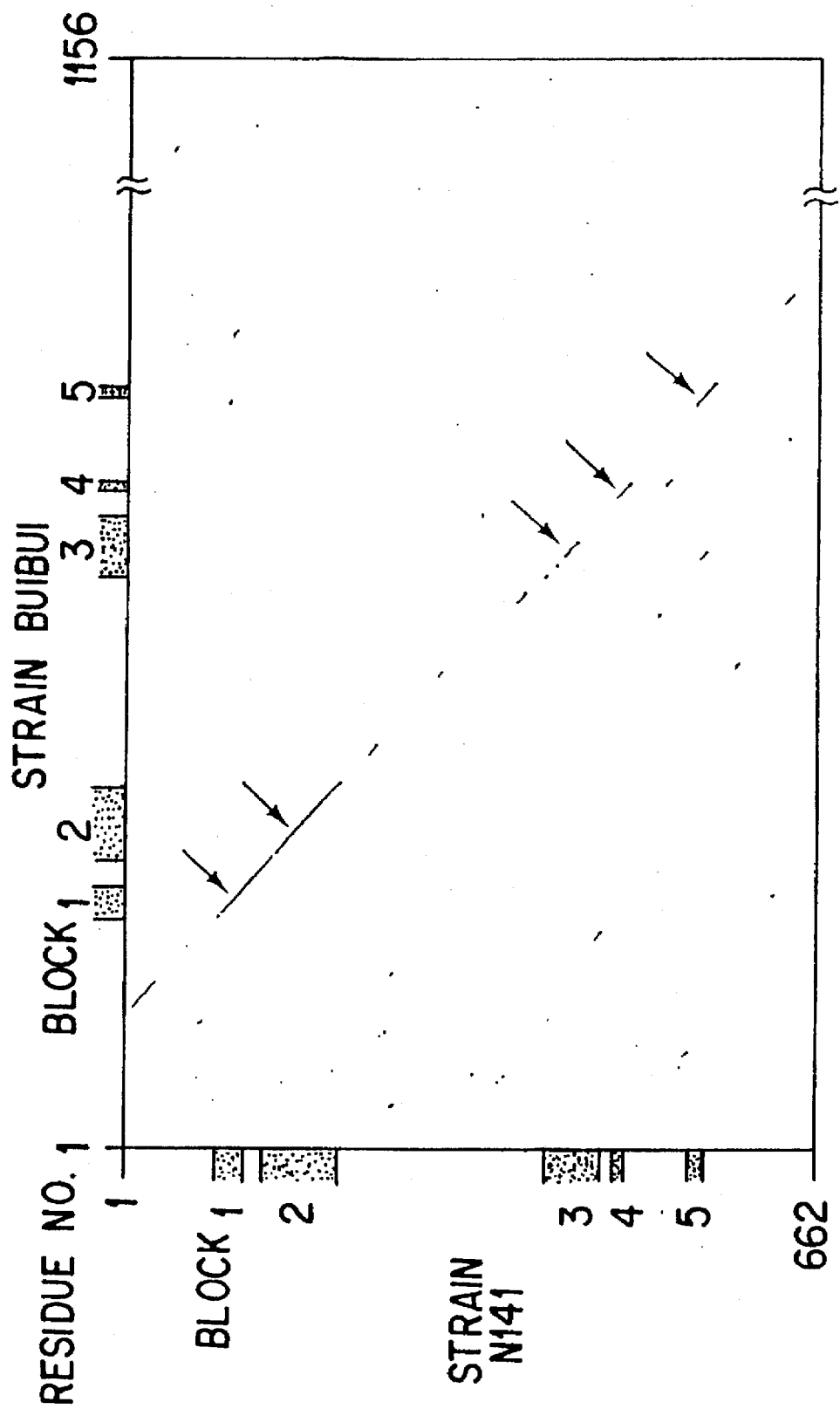
FIG. 2 shows a comparison of homology between the N-terminal 662 amino acids encoded by *Bacillus thuringiensis* var. *japonensis* N141 gene and the amino acid sequence encoded by *Bacillus thuringiensis buibui* gene.

Gene: Using antibodies raised by immunizing guinea pig with the crystal protein of about 130,000 daltons produced by this strain, screening was effected to clone a gene coding for the N141 crystal protein, hereinafter abbreviated as N141 gene. This gene has 3,759 bases and contains a translational region in from 47 to 3,556. Further, as compared with the known *japonensis buibui* gene having an activity against coleopterous insects (Japanese Patent Application Laying-open No. 65292/1994), this gene has only about 60% of homology in the amino acid sequence level with the known gene as shown in FIG. 2.

From these, the N141 of the present invention is distinguished from known strains and therefore is novel.

N141 strain may be cultivated using known standard media and fermentation methods. Carbon sources may include sucrose, maltose, glucose, fructose, molasses and soluble starch.

Nitrogen sources may include ammonium sulfate, ammonium chloride, cottonseed powder, yeast extract, soybean cake and casein hydrolysate. Minerals and vitamins may be supplied from organic carbon sources or nitrogen sources, such as molasses and yeast extract, and optionally inorganic salts and vitamins may be further added. The cultivation may preferably be carried out at a pH of 5 to 8 and a temperature of 25° to 30° C. for 2 to 5 days in a stirred and aerated system under aerobic conditions.

After cultivation, the insecticidal crystal protein may be isolated from the culture medium in a conventional manner such as centrifugation or filtration.

The N141 crystal protein may be employed as an active ingredient in a harmful organism controlling agent for use in controlling coleopterous and lepidopterous insects. However, the N141 strain itself may also be employed as a crystal toxin-containing ingredient without isolation of the crystalline protein.

When the crystal toxin-containing ingredient is used in a harmful organism controlling agent, it may generally be mixed with a suitable carrier, including a natural mineral fiber such as talc or kaolin, a solid carrier such as diatomaceous earth, or a liquid carrier such as water, and optionally an emulsifier, dispersant, suspending agent, penetrant, spreader and/or stabilizer may be added to formulate into any practical dosage form such as wettable powder, dust, granule or flowable agent.

Optionally, the agent may be formulated or sprayed together with other herbicide, pesticide, fungicide, plant growth-regulator, synergist, attractant, plant nutrient and/or fertilizer so long as they do not interfere with the crystalline toxin.

According to the present invention, the amount of the crystal toxin-containing ingredient applied may vary depending upon an application site, time and method, a pest to be controlled, and a crop to be protected; however, the amount of effective ingredient applied may usually about 0.1 to 99% by weight, preferably about 0.5 to 50% by weight of the agent.

Amounts of various ingredients in the agent of the present invention are exemplified below:

|  | Effective ingredient | Carrier | Surfactant | Auxiliary ingredients |
|---|---|---|---|---|
| Wettable powder | 1–70 | 15–93 | 3–10 | 0–5 |
| Dust | 0.01–30 | 67–99.5 |  | 0–3 |
| Granule | 0.01–30 | 67–99.5 |  | 0–8 |
| Flowable agent | 1–70 | 10–90 | 1–20 | 0–10 |

All the amounts shown in the above Table are % by weight.

When applied, a wettable powder or flowable agent is diluted with a predetermined amount of water before spraying while a dust or granule is directly sprayed without dilution with water.

Examples of each ingredient used in the agent may be as follows:

| (Wettable powder) | |
|---|---|
| Effective ingredient: | the crystal toxin-containing material according to the present invention; |
| Carrier: | calcium carbonate, kaolinite, Zeeklite D, Zeeklite PEP, diatomaceous earth, talc; |
| Surfactant: | Sorpol, calcium lignin sulfonate, Lunox; |
| Other ingredients: | Carplex # 80. |
| (Dust) | |
| Effective ingredient: | the crystal toxin-containing material according to the present invention; |
| Carrier: | calcium carbonate, kaolinite, Zeeklite D, diatomaceous earth, talc; |
| Other ingredients: (Granule) | diisopropyl phosphate, Carplex # 80. |
| Effective ingredient: | the crystal toxin-containing material according to the present invention; |
| Carrier: | wheat flour, wheat bran, corn grits, Zeeklite D, |
| Other ingredients: (Flowable agent) | paraffin, soybean oil. |
| Effective ingredient: | the crystal toxin-containing material according to the present invention; |
| Carrier: | water; |
| Surfactant: | Sorpol, sodium lignin sulfonate, Lunox, Nippol; |
| Other ingredients: | ethylene glycol, propylene glycol. |

Formulation examples of the harmful organism controlling agent comprising the crystal toxin-containing material according to the present invention as an effective ingredient are given below but the present invention is not limited thereto. All parts are by weight.

| Formulation Example 1: Wettable powder | |
|---|---|
| crystal toxin-containing material according to the present invention | 25 parts |
| Zeeklite PEP (mixture of kaolinite and sericite; Zeeklite Industry Co.; trade name) | 66 parts |
| Sorpol 5039 (anionic surfactant; Toho Chemical Co.; trade name) | 4 parts |
| Carplex # 80 (white carbon; Shionogi Pharmaceutical Co.; trade name) | 3 parts |
| Calcium lignin sulfonate | 2 parts |

The above ingredients are homogeneously mixed and pulverized to yield a wettable powder.

Upon application, the wettable powder is diluted 500 to 2,000 times and sprayed so that the amount of crystal toxin-containing ingredient applied is 0.1 to 5 kg per hectare.

| Formulation Example 2: Dust | |
|---|---|
| crystal toxin-containing material according to the present invention | 3.0 parts |
| clay | 95 parts |
| diisopropyl phosphate | 1.5 parts |
| Carplex # 80 (white carbon; Shionogi Pharmaceutical Co.; trade name) | 0.5 parts |

The above ingredients are homogeneously mixed and pulverized to yield a dust.

Upon application, the dust is sprayed so that the amount of crystal toxin-containing ingredient applied is 0.1 to 5 kg per hectare.

| Formulation Example 3: Flowable agent | |
|---|---|
| crystal toxin-containing material according to the present invention | 35 parts |
| Lunox 1000C (anionic surfactant; Toho Chemical Co.; trade name) | 0.5 parts |
| Sorpol 3353 (nonionic surfactant; Toho Chemical Co.; trade name) | 10 parts |
| 1% aqueous Xanthane gum solution (natural highpolymer) | 20 parts |
| water | 34.5 parts |

The above ingredients except the crystal toxin-containing ingredient of the present invention are homogeneously dissolved, mixed with the crystal toxin-containing material, thoroughly stirred and wet-pulverized in a sand mill to yield a flowable agent.

Upon application, the flowable agent is diluted 50 to 2,000 times and sprayed so that the amount of crystal toxin-containing ingredient applied is 0.1 to 5 kg per hectare.

The method of protecting a plant from damage caused by lepidopterous and/or coleopterous pests according to the present invention generally comprises treating, e.g., by spraying, a plant infected or suspected to be infected with the pest, with the harmful organism controlling agent diluted with a diluent such as water. The effective ingredient of the controlling agent is a toxic δ-endotoxin. If desired, the toxic δ-endotoxin may be applied in an isolated form separately from a bacterium producing the toxin to the plant or infectious pest. Generally, however, it is not necessary to isolate the crystalline protein from the bacterium.

Pests which may be destroyed by the method of the present invention include insects of the order Lepidoptera or Coleoptera.

Lepidopterous insects may include armyworms, such as common cutworm (*Spodoptera litura*), beat armyworm (*Spodoptera exigua*) and cabbage armyworm (*Mamestra brassicae*); diamondback moth (*Plutella xylostella*), rice leafroller (*Cnaphalocrocis medinalis*), rice stem borer (*Chilo suppressalis*), rice skipper (*Parnara guttata*), common white (*Pieris rapae crucivora*), oriental moth (*Monema flavescens*) and common yellow swallowtail (*Papilio machaon hippocrates*).

Coleopterous insects may include grubs, such as cupreous chafer (*Anomala cuprea*), *Anomala schonfeldti*, soybean beetle (*Anomala rufocuprea*), Asiatic garden beetle (*Maladera castanea*), chestnut brown chafer (*Adoretus tenuimaculatus*) and Japanese beetle (*Popillia japonica*); lady beetlest such as 28-spotted ladybird (*Epilachna vigintioctopunctata*) and large 28-spotted ladybird (*Epilachna vigintioctomaculata*); weevils, such as rice water weevil (*Lissorhoptrus oryzophilus*), *Scepticus griseus*, sweetpotato weevil (*Cylas formicarius*), hunting billbug (*Sphenophrus venatus vestius*) and maize weevil (*Sitophilus zeamaise*); leaf beetles, such as striped flea beetle (*Phyllotreta striolata*) and cucurbit leaf beetle (*Aulacophora femoralis*); click beetles, such as *Melanotus okinawaensis*; longicom beetles, such as Japanese pine sawer (*Monochamus alternatus*) and sesame-spotted longicom beetle (*Mesosa myops*); bark beetles, such as Japanese bark beetle (*Scolytus japonicus*) and alnus ambrosia beetle (*Xylosandrus germanus*); flour beetles, such as yellow mealworm (*Tenebrio molitor*) and red flour beetle (*Tribolium castaneum*).

The method of the present invention may be used to protect a wide variety of plants which are subject to infection with lepidopterous or coleopterous insect pests. The plants to be protected by the method of the present invention include vegetables such as cabbage and cauliflower, fruit trees such as citrus and apples, grains such as rice, wheat and beans, stored grains, stored foods, lawn in golf courses and gardens, industrial crops such as tea and sugarcane, as well as flower. Also, trees in non-crop lands such as parks and forests.

N141 gene may be isolated from N141 strain. The whole DNA of N141 strain may be digested with one or more restriction enzymes and the resulting DNA fragments may be size-fractionated into DNA fractions of 2 to 5 Kbp. The fractions may be ligated to a suitable vector and used to transform *Escherichia coli*. A transformed *E. coli* possessing a desired gene may be identified by enzyme immunoassay using antibodies against the N141 crystal protein.

The N141-derived crystal protein gene DNA thus identified may be treated with a suitable restriction enzyme and the resulting DNA fragment is ligated to a suitable cloning vector to make a gene cassette.

The gene cassette may be used to transform a microorganism, such as *E. coli*, and the base sequence of N141 crystal gene may then be determined by gene analysis methods such as dideoxy method.

Further, the gene cassette may also be used to transform a gram-positive bacterium having an insecticidal activity, such as Bt. Thus, a transformed Bt may be produced which is effective to control a wider variety of insects.

To express the N141 gene in a plant, a suitable restriction site may be introduced into both sides of each gene or a portion thereof in the gene cassette. This may be carried out by site-directed mutagenesis.

The portion of N141 gene coding for an insecticidally effective portion of N141 protein may be inserted into the nuclear genome of a single plant cell in a stable manner and the thus transformed cells may be used to produce a transformed plant which is resistant to insects.

The thus transformed plant may be used to produce transformed plants having the same properties, or the insecticidally effective portion of N141 gene may be introduced into other varieties of the same or related plant species. A seed produced from the transformed plant contains the insecticidally effective portion of N141 gene as a stable genome insert.

The N141 strain may further be transformed with a foreign Bt gene having one or more insecticidal activities, whereby a transformed N141 strain may be produced which is useful for destroying a wider variety of pests.

The N141 crystal protein may be used to immunize guinea pig to prepare an antibody specific to this crystal protein.

In the protected area, i.e., in the area to which N141 strain and/or N141 crystal protein has been applied, certain insects will ingest the N141 strain and/or N141 crystal protein or mixture thereof, or transformed plants and/or microorganisms incorporating the N141 gene, and as a result they are killed or injured by the N141 crystal protein.

EXAMPLES

The present invention will be further illustrated by the following examples but is not limited thereto.

Example 1

Isolation and properties of N141 strain

N141 strain was isolated from soil taken in Saitama, Japan.

Ten mg of a soil sample was placed in an Erlenmeyer flask and 10 mL of sterilized water was injected thereinto. The flask was shaken for 30 minutes and allowed to stand for some time. Two mL of the supernatant was taken out and immediately heated at 80° C. for 10 minutes. The heated solution was then diluted in two steps, 10 times and 100 times, respectively. Each solution (1 mL) of the ×10 and ×100 diluted solutions was incubated on an NB plating medium (8.4 g NUTRIENT BROTH, 20 g agar per liter of sterilized water) at 30° C. for 24 to 48 hours.

Features of the novel strain N141

Colony formation: An opaque white colony with an irregular border.

Cell morphology in the growth phase: Typical of Bt.

Serotype of H-antigen: 23, *japonensis*.

Intracellular component: A sporulating cell produces an amorphous crystal protein. The electron microscopic photograph of the crystal protein is shown in FIG. 1.

Alkali-soluble protein: This strain has a protein which runs to about 130,000 daltons on electrophoresis.

Activity: This strain has an insecticidal activity against lepidopterous and coleopterous pests tested.

Gene: Using antibodies raised by immunizing guinea pig with the crystal protein of about 130,000 daltons produced by this strain, screening was effected to clone a gene coding for the N141 crystal protein, hereinafter abbreviated as N141 gene. This gene has 3,759 bases and contains a translational region in from 47 to 3,556. Further, as compared with the known *japonensis buibui* gene having an activity against coleopterous insects (Japanese Patent Application Laying-open No. 65292/ 1994), this gene has only about 60% of homology in the amino acid sequence level with the known gene as shown in FIG. 2.

Example 2

Storage and sterilization of N141 strain

Desirably, for longtime storage of N141 strain, N141 is subjected to rotary shaking culture with NB liquid medium (8.4 g NUTRIENT BROTH per liter of sterilized water) at 30° C. and 150-200 rpm for 24 to 72 hours and equal amounts of the culture medium and glycerol are mixed and stored at −80° C., or alternatively, said culture medium is centrifuged and the resulting cells are suspended in a protective liquid (10% skim milk, 1% sodium glutamate) and dried under vacuum.

Sterilization of N141 strain is carried out in an autoclave at ° C. for 20 minutes.

Example 3

Purification of crystal protein of N141 strain

A platinum loopful of N141 strain was inoculated in a test tube containing 5 mL of NB liquid medium (8.4 g NUTRIENT BROTH per liter of sterilized water) and reciprocal shaking culture was carried out at 30° C. for 12 to 24 hours to yield a seed culture. The seed culture was inoculated in a 500 mL Erlenmeyer flask containing 100 ml of NB liquid medium (8.4 g NUTRIENT BROTH per liter of sterilized water) in a final concentration of 1% and shaking culture was effected at 30° C. and 150 rpm for 72 to 96 hours. Thereafter, cells, spores and crystal proteins were collected by centrifugation. A suitable amount of buffer (Tris-HCl, NaCl, EDTA) was added to the resulting precipitate and the mixture was subjected to ultrasonication to yield a suspension.

Example 4

Properties of N141 crystal protein

The suspension obtained in Example 3 was subjected to electrophoresis on 8% SDS-PAGE gel to investigate an electrophoretic pattern. Also, western blotting analysis was carried out using antibodies. As a result, it was revealed that N141 strain produces a crystal protein with a molecular weight of about 130,000 daltons.

Example 5

Insecticidal activity of N141 strain against cupreous chafer (*Anomala cuprea*)

The suspension prepared in Example 3 was diluted to a predetermined concentration and a spreader was added thereto. The thus prepared sample solution was mixed into leaf mould which had previously sterilized, and cupreous chafer (*Anomala cuprea*) was released. As a result of observation, an insecticidal activity against cupreous chafer (*Anomala cuprea*) was recognized.

Example 6

Insecticidal activity of N141 strain and N141 crystal protein against diamondback moth (*Plutella xylostella*)

The suspension prepared in Example 3 was diluted to a predetermined concentration and a spreader was added thereto to prepare a sample solution. A leaf of cabbage was immersed into the sample solution, air-dried thoroughly and placed into a styrol cup containing a wet filter paper. Larvae of diamondback moth (*Plutella xylostella*) in the middle of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 1.

TABLE 1

Insecticidal activity of N141 strain and N141 crystal protein against larvae of diamondback moth (*Plutella xylostella*) in the middle of 3 larval instars stage

| Concentration (ppm) | Mortality (%) |
| --- | --- |
| 10000 | 100 |
| 3000 | 100 |
| 1000 | 100 |
| 100 | 50 |

Example 7

Insecticidal activity of N141 strain and N141 crystal protein against *Bombyx mori*

The suspension prepared in Example 3 was diluted to a predetermined concentration and a spreader was added thereto to prepare a sample solution. A leaf of mulberry was immersed into the sample solution, air-dried thoroughly and placed into a styrol cup containing a wet filter paper. Larvae of *Bombyx mori* on the second day of of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 2.

TABLE 2

Insecticidal activity of N141 strain and N141 crystal protein against larvae of *Bombyx mori* on the second day of 3 larval instars stage

| Concentration (ppm) | Mortality (%) |
| --- | --- |
| 3000 | 100 |
| 1000 | 95 |
| 100 | 50 |

Example 8

Isolation of N141 gene The whole DNA was prepared from *N*141 strain and partially digested with EcoRI. The digested DNAs were fractionated and DNA fragments of about 2 to 5 Kbp were ligated to a phage vector λgt11 digested with EcoRI. These vectors were used to transform *E. coli*. The recombinant *E. coli* clones were screened with antibodies raised by immunizing guinea pig with about 130 kDa protein which was assumed to be N141 crystal protein, to identify clones containing N141 gene. DNAs were prepared from the identified recombinant *E. coli* clones and digested with restriction enzyme EcoRI. The digested DNA fragments were subjected to electrophoresis on 0.8% agarose gel to identify an inserted DNA fragment of about 3.4 Kbp.

Example 9

Cloning of N141 gene

Figure 3:
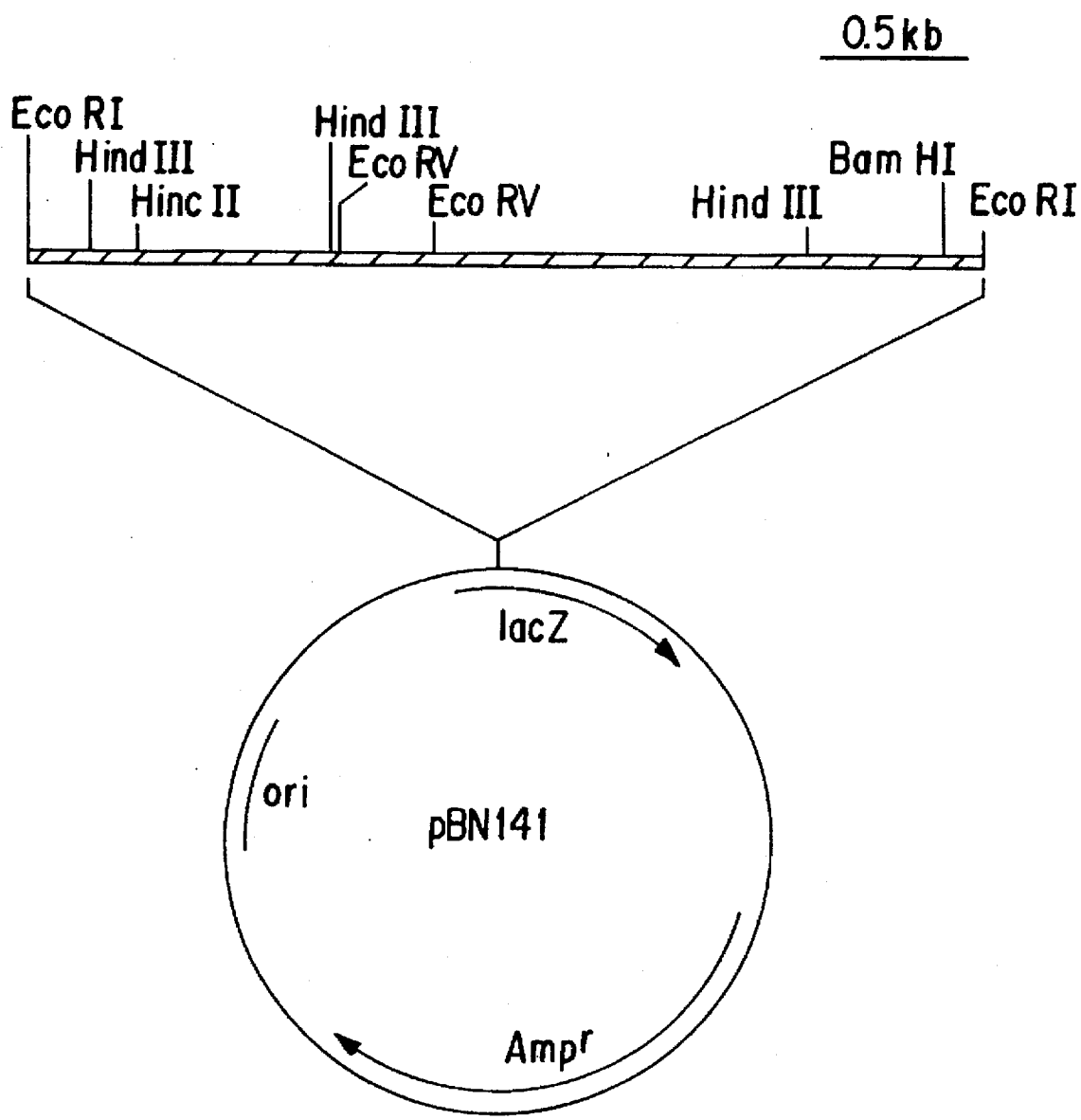
FIG. 3 depicts the cassette pBN141 comprising *Bacillus thuringiensis* var. *japonensis* N141 gene inserted into a vector.

The DNA fragments prepared in Example 8 were fractionated and ligated to a plasmid vector Bluescript II SK (−) digested with EcoRI so as to construct a gene cassette (pBN141; FIG. 3). This pBN141 was not of full length and cloning was again repeated. The base sequence of a DNA fragment containing a full length N141 gene was determined by the dideoxy method.

Example 10

Base and amino acid sequences of N141 gene

The base sequence consisted of 3759 bases as shown in SEQ ID NO:1. The open reading frame (ORF) consisted of 3510 bases, i.e. from 47th to 3556th bases, and coded for 1169 amino acids (the 1170th base being a termination codon). The amino acid sequence of the N-terminal 662 amino acids of this N141 protein was compared with those of a protein encoded by the known *japonensis buibui* gene which shows an activity against coleopterous insects (Japanese Patent Application Laying-open No. 65292/1994). It was found that the two genes had a homology in the amino acid level of only about 60% as shown in FIG. 2.

Example 11

Expression of N141 Crystal protein in *E. coli* DH5α

To produce the crystal protein from N141 gene, the gene cassette pBN141 was used to transform *E. coli* DH5α. The resulting recombinant *E. coli*, hereinafter referred to as *E. coli*:DH5α (pBN141), was incubated in LB-amp liquid medium (10 g Trypton, 10 g NaCl, 5 g Yeast extract, 0.2% glucose, 50 mg ampicillin per liter of sterilized water) at 37° C. for about 3 hours. IPTG was added to a final concentration of 1 mM and further incubated at 37° C. for 20 hours. After culture, the culture medium was centrifuged and 4 unit volumes of Lysis buffer were added to unit weight of the precipitate to suspend at room temperature for 10 hours. Then, Lysozyme was added and mixed in a final concentration of 1 mg/mL and allowed to stand on ice for 10 minutes. Further, Triton X-100 was added and mixed in a final concentration of 1% and allowed to stand at room temperature for 10 minutes. After centrifugation the supernatant was recovered.

Example 12

Properties of protein expressed in *E. coli*:DH5α (pBN141)

The supernatant obtained in Example 11 was subjected to electrophoresis on 8% SDS-PAGE gel and to western blotting using antibodies. As a result, it was confirmed that *E. coli*:DH5α (pBN141) produced N141 crystal protein.

Example 13

Insecticidal activity of the protein expressed in *E. coli*:DH5α (pBN141) against larvae of diamondback moth (*Plutella xylostella*)

To the supernatant solution obtained in Example 11, a spreader was added and diluted to prepare a sample solution. A leaf of cabbage was immersed into the sample solution, air-dried thoroughly and placed into a styrol cup containing a wet filter paper. Larvae of diamondback moth (*Plutella xylostella*) in the middle of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 3.

TABLE 3

| Insecticidal activity of the protein expressed in *E. coli*:DH5α (pBN141) against larvae of diamondback moth (*Plutella xylostella*) in the middle of 3 larval instars stage | |
|---|---|
| Concentration (ppm) | Mortality (%) |
| 200 | 85 |
| 100 | 50 |

Example 14

Insecticidal activity of the protein expressed in *E. coli*:DH5α (pBN141) against larvae of *Bombyx mori*

To the supernatant solution obtained in Example 11, a spreader was added and diluted to prepare a sample solution. A leaf of mulberry was immersed into the sample solution, air-dried thoroughly and placed into a styrol cup containing a wet filter paper. Larvae of *Bombyx mori* on the second day of of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 4.

TABLE 4

| Insecticidal activity of the protein expressed in *E. coli*:DH5α (pBN141) against larvae of *Bombyx mori* on the second day of 3 larval instars stage | |
|---|---|
| Concentration (ppm) | Mortality (%) |
| 200 | 70 |

While the above examples are directed to only several embodiments of the present invention, it is apparent to those skilled in the art that many other modifications and/or changes are contemplated in the present invention. For example, any peptide having an insecticidal activity and coding for an amino acid sequence which is different from that represented by SEQ ID NO:2 in that one or more amino acids may be added, deleted and/or replaced, as well as any DNA coding for such a modified peptide are included within the scope of the present invention.

The N141 crystal protein of the present invention has an activity not only against lepidopterous insects but also coleopterous insects such as cupreous chafer (*Anomata cupreal*) and is expected to be useful for insecticidal compositions.

What is claimed is:

1. An insecticidal crystal protein produced by *Bacillus thuringiensis* var. *japonensis* strain N141 having the amino acid sequence of SEQ ID NO:2.

2. An insecticidal composition comprising the protein of claim 1.

3. A method of protecting a plant from damage caused by a pest which comprises applying a protein of claim 1 to said plant.

4. The method of claim 3, wherein the pest is a lepidopterous or coleopterous insect.

* * * * *